US008685032B2

(12) United States Patent  
Melsheimer

(10) Patent No.: US 8,685,032 B2
(45) Date of Patent: Apr. 1, 2014

(54) PRESSURE SENSING VERTEBROPLASTY EXTENSION TUBE

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 335 days.

(21) Appl. No.: 13/027,716

(22) Filed: Feb. 15, 2011

(65) Prior Publication Data

US 2011/0208203 A1 Aug. 25, 2011

Related U.S. Application Data

(60) Provisional application No. 61/307,010, filed on Feb. 23, 2010.

(51) Int. Cl.
*A61M 5/48* (2006.01)

(52) U.S. Cl.
USPC .............................. 606/94; 604/131; 604/240

(58) Field of Classification Search
USPC ................. 606/92–94; 604/82–92, 131–155, 604/240–243; 222/386, 386.5, 325–328; 73/700, 730
See application file for complete search history.

(56) References Cited

U.S. PATENT DOCUMENTS

| | | | |
|---|---|---|---|
| 3,590,640 A | 7/1971 | Cindrich | |
| 3,736,899 A | 6/1973 | Manske | |
| 3,994,598 A | 11/1976 | Reytblatt | |
| 4,426,881 A * | 1/1984 | Magoulick | 73/146.8 |
| 4,939,368 A | 7/1990 | Brown | |
| 6,442,316 B1 | 8/2002 | Rossi et al. | |
| 6,587,211 B1 | 7/2003 | Gelbart | |
| 6,856,399 B2 | 2/2005 | Kuskovsky et al. | |
| 2009/0264942 A1 * | 10/2009 | Beyar et al. | 606/86 R |

FOREIGN PATENT DOCUMENTS

WO  WO 2011/054110 A1 * 5/2011 ............... A61F 2/46

OTHER PUBLICATIONS

Internet Pages, "Prescale:Features," www.fujifilm.com/products/prescale/prescalefilm/features, printed Jan. 13, 2010, 3 pages.
Internet Pages, "Tactile Pressure Indicating Sensor Film," www.sensorprod.com/pressurex.php, printed Jan. 13, 2010, 2 pages.
Product brochure, "Tactile Pressure Indicating Sensor Film," Sensor Products, Inc., Jan. 4, 2010, 2 pages.

\* cited by examiner

*Primary Examiner* — Todd Manahan
*Assistant Examiner* — Jessica Weiss
(74) *Attorney, Agent, or Firm* — Woodard, Emhardt, Moriarty, McNett & Henry LLP

(57) ABSTRACT

Disclosed in certain embodiments is a pressure sensing tube for transporting a material under pressure through a lumen and a pressure sensitive material associated with the tube and operable to change in appearance in response to a physical change in the tube caused by pressure within the lumen.

A method of manufacturing a pressure sensing tube is also disclosed.

20 Claims, 6 Drawing Sheets

PRESSURE SENSING VERTEBROPLASTY EXTENSION TUBE

This application claims the benefit of U.S. Provisional Application No. 61/307,010, filed Feb. 23, 2010, which is hereby incorporated by reference.

BACKGROUND

The present disclosure concerns medical devices and methods useful for vertebroplasty and other medical injections.

As further background, during vertebroplasty procedures, bone cement is injected under high pressure into a compromised vertebral body to stabilize it. Excessive injection pressure can contribute to fracturing already weakened vertebrae that could cause bone fragments to impinge upon nerves or blood vessels.

During vertebroplasty procedures, an extension tube may be used to keep the interventionalist out of the x-ray field. This extension tube can be connected between the intraosseous needle or catheter in the vertebral body and the high-pressure injection mechanism controlled by the interventionalist (outside of the x-ray field).

It can be difficult to monitor the pressure in the injection apparatus because the cement used in vertebroplasty procedures is constantly in the process of setting-up, leaving only a few minutes to complete an injection, potentially with varying injection pressure requirements over time as the cement sets-up. Dead-end pressure indicators such as gages may not accurately portray the pressures exerted by viscous cement as it starts to set-up. Conversely, the extension tube is generally exposed to the same pressure fluctuations as the viscous cement passing therethrough.

Needs exist for improved or alternative medical devices for monitoring injection pressure in vertebroplasty and other medical procedures to ensure that injection pressures do not become excessive.

SUMMARY

In certain aspects, the present disclosure relates to a pressure sensing tube that includes a tube for transporting a material under pressure through a lumen and a pressure sensitive material associated with the tube and operable to change in appearance in response to a physical change in the tube caused by pressure within the lumen. In certain embodiments, the pressure sensing tube includes an inner tube that defines a lumen and is sufficiently compliant or otherwise deformable that a change in the pressure in the lumen changes the shape (e.g. diameter) of at least a portion of the inner tube, an outer member, and a pressure sensitive material positioned between the inner tube and the outer member. The pressure sensitive material changes in appearance in response to the change in shape, for instance by expansion of the inner tube or portion thereof and restraint by the outer member. The components of the pressure sensing tube can be constructed and arranged such that the appearance of the pressure sensitive material changes when the pressure within the lumen of the inner tube exceeds a predetermined limit.

Among other things, there is disclosed an injection assembly having an injection apparatus operable to eject a viscous fluid, and a pressure sensing extension tube coupled to the injection apparatus. The extension tube includes in certain embodiments an inner tube defining a first lumen, the inner tube being deformable in response to a change in pressure in the first lumen, an outer member, and a pressure sensitive material positioned between the inner tube and the outer member. The pressure sensitive material is adapted or operable to display a differing visual appearance when compressed between the inner tube and the outer member.

Embodiments can include an outer member that is less compliant than the inner tube. The inner tube and the outer member may be configured and arranged such that the differing visual appearance correlates to a predetermined first lumen pressure, which is greater than 3000 psi in some embodiments. The injection apparatus may be configured and arranged as a bone cement injector and the pressure sensing extension tube is configured and arranged as a vertebroplasty extension tube. The outer member can have a translucent portion, with the pressure sensitive material positioned under the translucent portion. The differing visual appearance is a change in color or hue in some embodiments, and the pressure sensitive material may be or include a pressure-indicating film. Embodiments are disclosed wherein the pressure-indicating film is bent along its longitudinally axis and positioned over the inner tube, or wherein the pressure-indicating film is spirally wrapped around the inner tube. The outer member may include translucent thermoplastic heat-shrink tubing shrunk over the inner tube and the pressure sensitive material.

Methods are also disclosed, including methods of manufacturing a pressure sensing vertebroplasty extension tube that include positioning a pressure sensitive material on the outer surface of a vertebroplasty extension tube having a first lumen that includes covering the pressure sensitive material and at least a portion of the vertebroplasty extension tube with an outer member, with the pressure sensitive material restrained between the outer surface of the vertebroplasty extension tube and the inner surface of the translucent outer member. The pressure sensitive material is adapted or operable to display a differing visual appearance when compressed between the inner tube and the outer member. Such methods may include spirally wrapping a pressure-indicating film around the outer surface of the vertebroplasty extension tube, and/or longitudinally rolling a pressure-indicating film around the outer surface of the vertebroplasty extension tube. Heat-shrinking a translucent thermoplastic heat-shrink outer member over the inner tube and the pressure sensitive material can also be performed. The pressure sensitive material can be positioned on a distal portion of the vertebroplasty extension tube. Additional or alternative steps can include configuring and arranging the vertebroplasty extension tube and the outer member such that the differing visual appearance correlates to a predetermined pressure in the first lumen, and selecting the outer member so that it has a compliance less than a compliance of the inner tube.

In some aspects, the present disclosure relates to a pressure sensing vertebroplasty extension tube. Embodiments of such a tube can include a vertebroplasty extension tube defining a lumen and including a first degree of deformability such that a change in pressure in the lumen changes the shape of the vertebroplasty extension tube. A pressure-indicating film is external of the vertebroplasty extension tube, and a translucent thermoplastic heat-shrink tube is over the pressure-indicating film (e.g. by shrinking), so that the pressure-indicating film is adapted or operable to visibly change when compressed between the heat-shrink tube and the extension tube. Such a heat-shrink tube can include a degree of compliance substantially less than that of the extension tube.

Additional aspects of the disclosure as well as features and advantages thereof will be apparent from the further descriptions herein.

DETAILED DESCRIPTION

Figure 1:
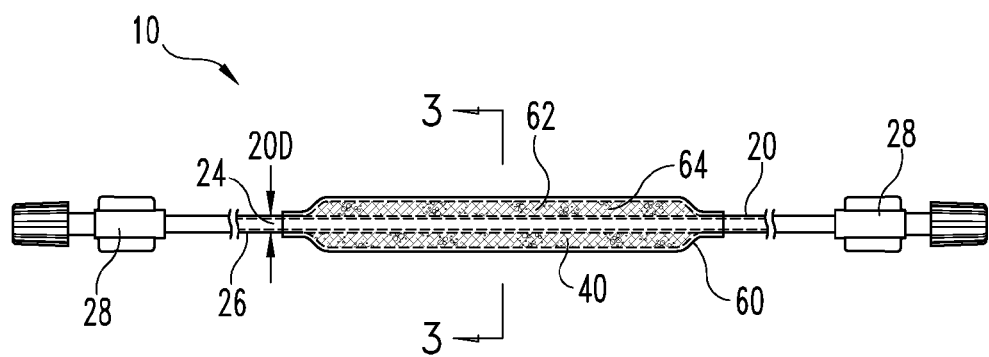
FIG. 1 is a side elevational cross-sectional view of a pressure sensing tube.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Figure 2:
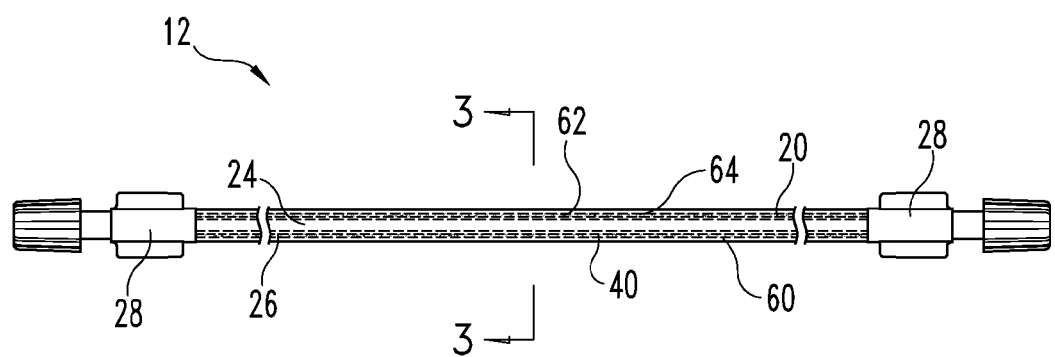
FIG. 2 is a side elevational cross-sectional view of an alternate embodiment of a pressure sensing tube.
Figure 3:
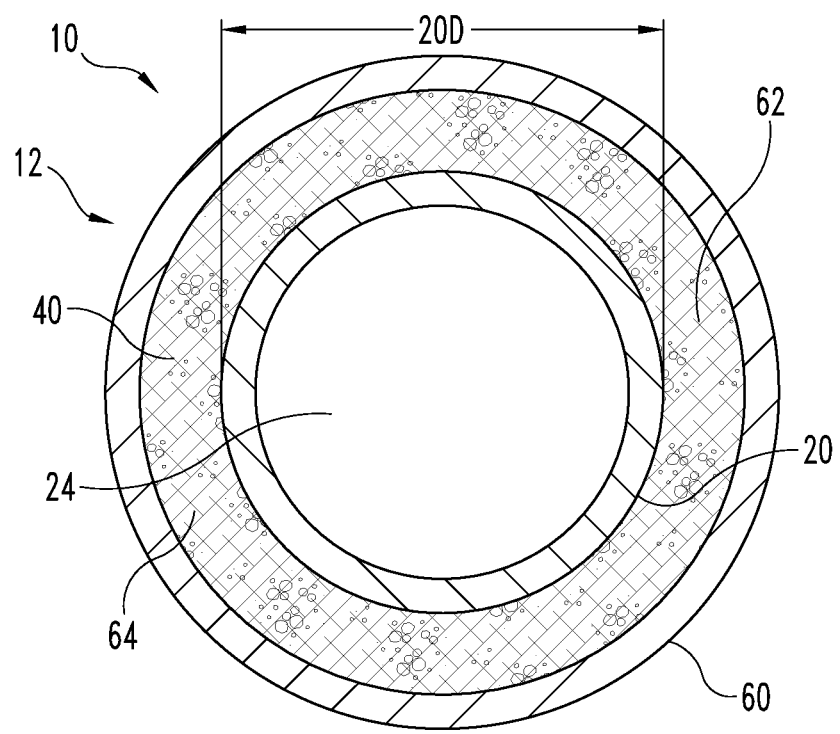
FIG. 3 is an end cross-sectional view of the FIG. 1 and FIG. 2 pressure sensing tube taken along line 3-3.

Referring to FIGS. 1-3, pressure sensing tubes 10 and 12 are illustrated. FIG. 1 includes a cross-sectional view of pressure sensing tube 10. FIG. 2 includes a cross-sectional view of pressure sensing tube 12. FIG. 3 is an end cross sectional view taken along the lines 3-3 in FIGS. 1 and 2. Pressure sensing tubes 10 and 12 include inner tube 20, pressure sensitive material 40 and outer member 60. Tube 20 includes lumen 24, wall 26 and connectors 28 on either end. Inner tube 20 has an outer diameter 20D. Inner tube 20 exhibits an ability to deform in response to pressure, permanently and/or reversibly, such that a change in pressure in lumen 24 changes the shape of outer diameter 20D to some degree including changing the size of inner tube 20. In certain embodiments, inner tube 20 can exhibit a degree of compliance in response to pressure within lumen 24 to facilitate this effect. Suitable polymers for use in forming (e.g. by extruding) tube 20 include, for example, polyamide (e.g. Nylon), polytetrafluoroethylene (e.g. Teflon), fluorinated ethylene-propylene (FEP), polyurethane, polyether block amide, or a mixture of these with each other or with other polymers.

Pressure sensitive material 40 is positioned between outer member 60 and inner tube 20 in interstitial space 64. Interstitial space 64 includes the portion of lumen 62 not occupied by inner tube 20. Pressure sensitive material 40 is a material operable to display a differing visual appearance when the pressure sensitive material 40 is compressed at or above a particular pressure. In one embodiment, pressure sensitive material 40 changes color or hue when pressure sensitive material is compressed above a particular pressure. In some embodiments, pressure sensitive material 40 may permanently change its visual appearance when a particular pressure is experienced, such as with a pressure-indicating film. Other embodiments of pressure sensitive material 40 could exhibit non-permanent visual appearance changes in response to pressure.

In one embodiment, pressure sensitive material 40 may be a pressure-indicating film. For example, such a material 40 may be or include PRESSUREX® supplied by Sensor Products, Inc. at 300 Madison Ave., Madison, N.J. 07940 USA. Alternatively, pressure sensitive material 40 may be or include PRESCALE® as supplied by Tekscan, Inc., 307 West First Street, S. Boston, Mass. 02127-1309 USA. Such pressure-indicating film can include mono-sheet and two-sheet configurations. In either case, the pressure-indicating film includes a base on which a color-developing material is coated and a layer of micro-encapsulated color-forming material positioned over the base layer. When sufficient pressure is applied, the microcapsules break and the color-forming material reacts with the color-developing material to change the color of the pressure-indicating film. With both PRESSUREX® and PRESCALE®, the color intensity of the film is proportional to the amount of pressure applied to the film. Both types of pressure-indicating film are supplied with varying sensitivities that respond to a wide range of pressures.

In the illustrated embodiment, pressure sensitive material 40 is positioned between outer member 60 and inner tube 20 in interstitial space 64. Pressure sensitive material 40 is thereby constrained between outer member 60 and inner tube 20 such that expansion of outer diameter 20D compresses or clamps pressure sensitive material 40 between outer member 60 and inner tube 20. This exerts pressure on pressure sensitive material 40 that may be sufficient to elicit the differing visual appearance of pressure sensitive material 40. This may be referred to herein as interstitial pressure.

In this regard, in certain embodiments, both inner tube 20 and outer member 60 are configured and arranged so that pressure sensitive material 40 changes in visual appearance when the pressure in lumen 24 exceeds a predetermined limit. For example, in one illustrative embodiment in which pressure sensing tube 10 or 12 is utilized as a vertebroplasty extension tube, the predetermined limit pressure in lumen 24 may exceed about 3000 pounds per square inch (psi), for example in some embodiments the predetermined limit pressure is in the range of approximately 3000 psi to approximately 5000 psi. The selected predetermined pressure in lumen 24 in such an embodiment may be varied based on anticipated strength of the compromised vertebral body in which injection is occurring (when used as vertebroplasty extension tube or other factors related to the injection environment). Pressure sensing tube 10 or 12 permits an interventionist to monitor high pressure injection situation while being located away from the injection site by observing whether the visual appearance of pressure sensitive material 40 changes due to pressure sensitive material 40 experiencing interstitial pressure when the pressure within lumen 24 exceeds the predetermined limit.

In some embodiments, outer member 60 exhibits a greater resistance to deformation (permanent and/or non-permanent) under pressure than inner tube 20, for example outer member 60 can exhibit a degree of compliance that is substantially less than the degree of compliance of inner tube 20 so that outer member 60 is more resistant to outward deflection compared to inner tube 20 when outer diameter 20D increases. This may result in a more dramatic increase in pressure experienced by pressure sensitive material 40 when outer diameter 20D changes shape. The degree of compliance or other deformation of inner tube 20 and outer member 60 can be selected based on the performance characteristics of pressure sensitive material 40 and the desired indicative pressure in lumen 24. In addition, in the illustrated embodiments, outer member 60 comprises a tubular structure. However, in alternative embodiments, outer member 60 can comprise any structure that constrains pressure sensitive material 40, including for example a segment or wall of a material, such as a polymeric material, laminated or otherwise attached to and circumscribing at least a portion of the outer circumference of inner tube 20 along part or all of the length of inner tube 20.

Referring to FIG. 1, the illustrated embodiment of pressure sensing tube 10 includes outer member 60 covering only a portion of inner tube 20. In one embodiment of pressure sensing tube 10, outer member 60 may comprise translucent thermal plastic heat-shrink tubing shrunk over inner tube 20 and pressure sensitive material 40. Heat-shrink tubing may be constructed with any suitable polymeric material, for example a polyamide (e.g. Nylon), polytetrafluoroethylene (e.g. Teflon), fluorinated ethylene-propylene (FEP), polyurethane, or polyether block amide, or a mixture of these with each other or with other polymers. While not illustrated, heat-shrink outer member 60 may further include an adhesive agent to bind outer member 60 to inner tube 20. In another embodiment, outer member 60 may comprise a portion of comparatively rigid tubing, for example rigid plastic, secured in position over pressure sensitive material 40 and comparatively flexible inner tube 20.

Referring to FIG. 2, the illustrated embodiment of pressure sensing tube 12 includes a substantially continuous outer member 60 covering inner tube 20. This embodiment of outer member 60 may comprise a continuous tube that covers the majority of the length of inner tube 20 of which all or a portion of is translucent or transparent to allow the observation of the visual characteristics of pressure sensitive material 40. Outer member 60 utilized with pressure sensing tube 12 may comprise a substantially homogenous material or may comprise a composite assembled from different components.

Figure 4A:
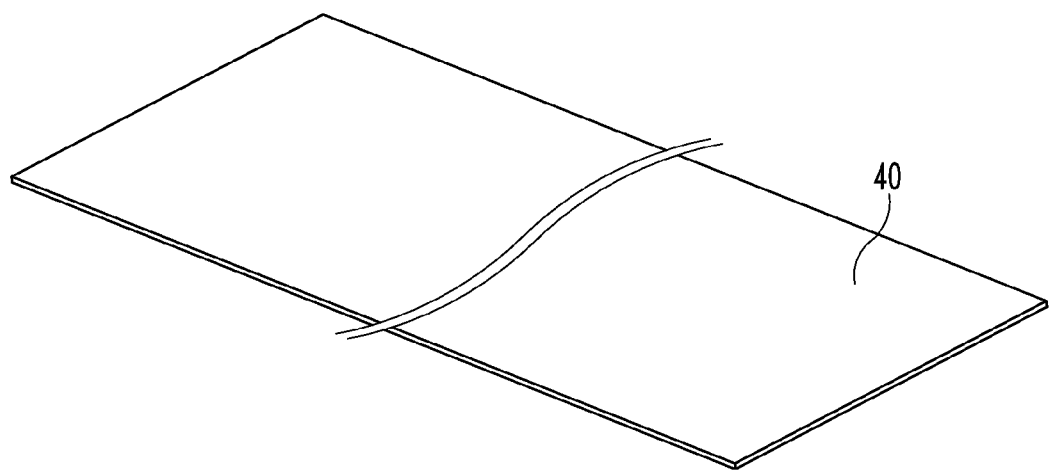
FIG. 4a is a perspective view of a pressure-indicating film.
Figure 4B:
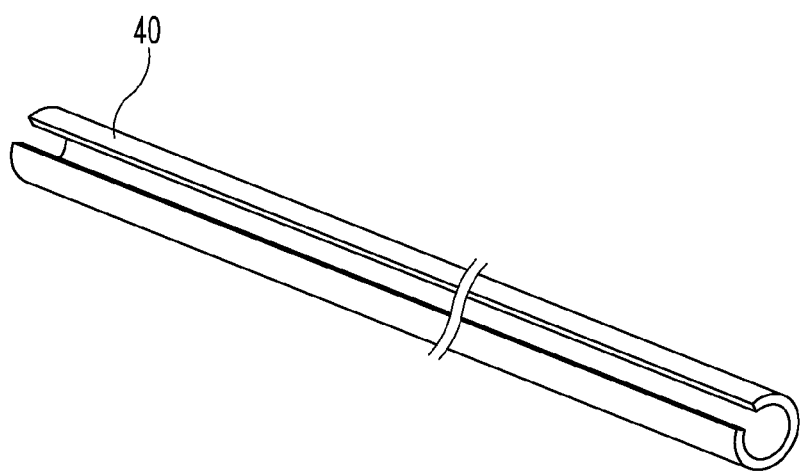
FIG. 4b is a perspective view of the FIG. 4a pressure sensing film bent along its longitudinal axis into a cylindrical shape.

Referring to FIGS. 4a and 4b, an embodiment of pressure sensitive material 40 is illustrated as pressure-indicating film. In FIG. 4b, pressure-indicating film 40 is bent along its longitudinal axis to form an approximate cylindrical shape.

Figure 5:
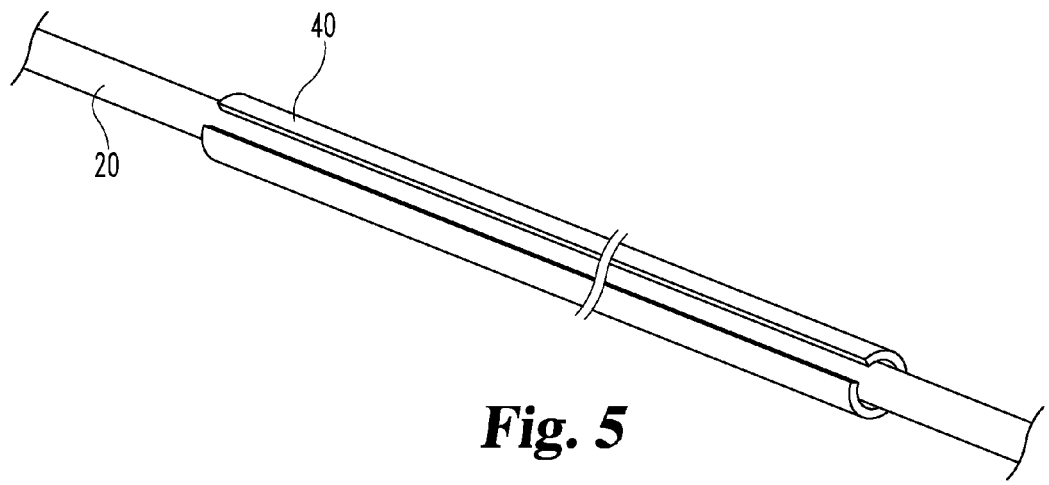
FIG. 5 is a partial assembly view of a pressure sensing tube including a tube surrounded by the pressure-indicating film of FIG. 4b.

Referring to FIG. 5, pressure-indicating film 40 is bent along its longitudinal axis and wrapped around inner tube 20 to approximate a cylindrical shape.

Figure 6:
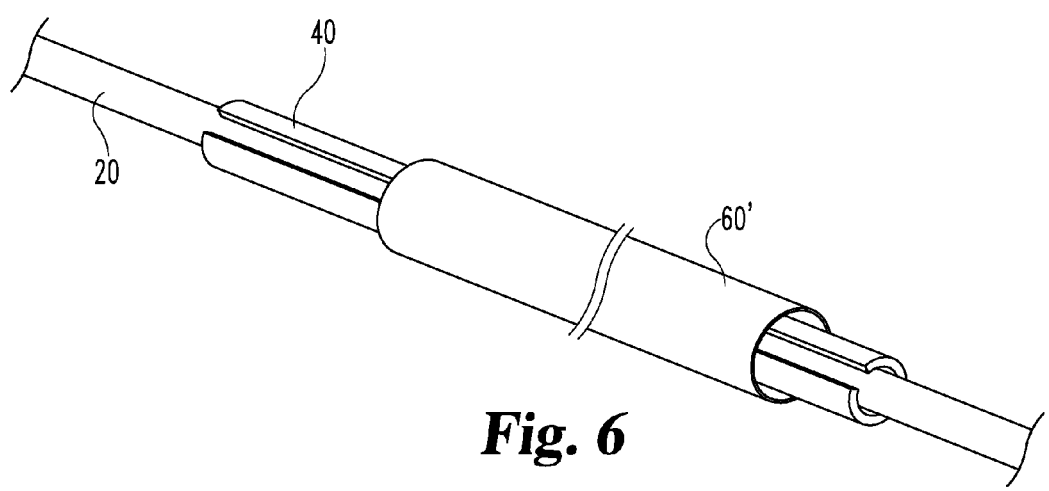
FIG. 6 is a partial assembly view of a pressure sensing tube including a tube, the pressure-indicating film of FIG. 4b and heat-shrink tubing surrounding both.

Referring to FIG. 6, an intermediate manufacturing configuration is illustrated including pressure-indicating film 40 bent along its longitudinal axis and wrapped around inner tube 20 with heat shrink tube 60' positioned above pressure-indicating film 40 in an expanded condition. Subsequent application of sufficient heat to heat shrink tube 60' will contract heat shrink tube 60' over pressure-indicating film 40 and inner tube 20 forming a configuration consistent with pressure sensing tube 10 illustrated in FIG. 1.

Figure 7:
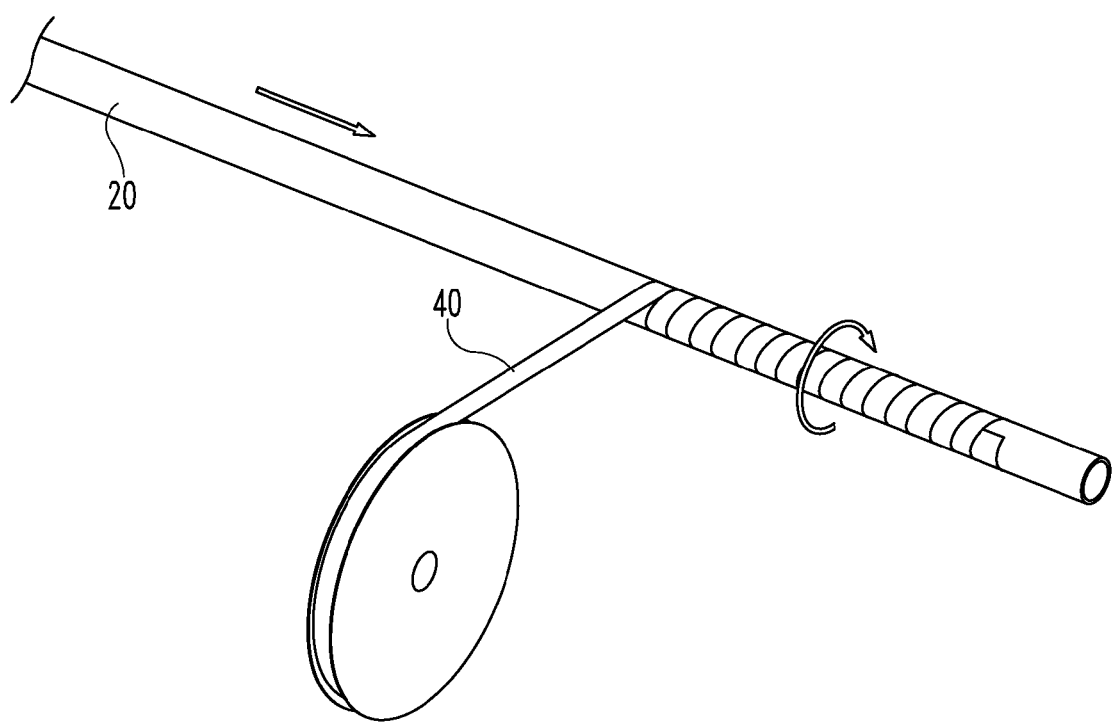
FIG. 7 is a partial assembly view of an alternate embodiment of the pressure sensing tube including a tube with pressuring indicating films spirally wrapped thereabout.

Referring to FIG. 7, an alternate assembly method is illustrated utilizing a ribbon like length of pressure-indicating film 40 spirally wrapped around inner tube 20.

Figure 8:
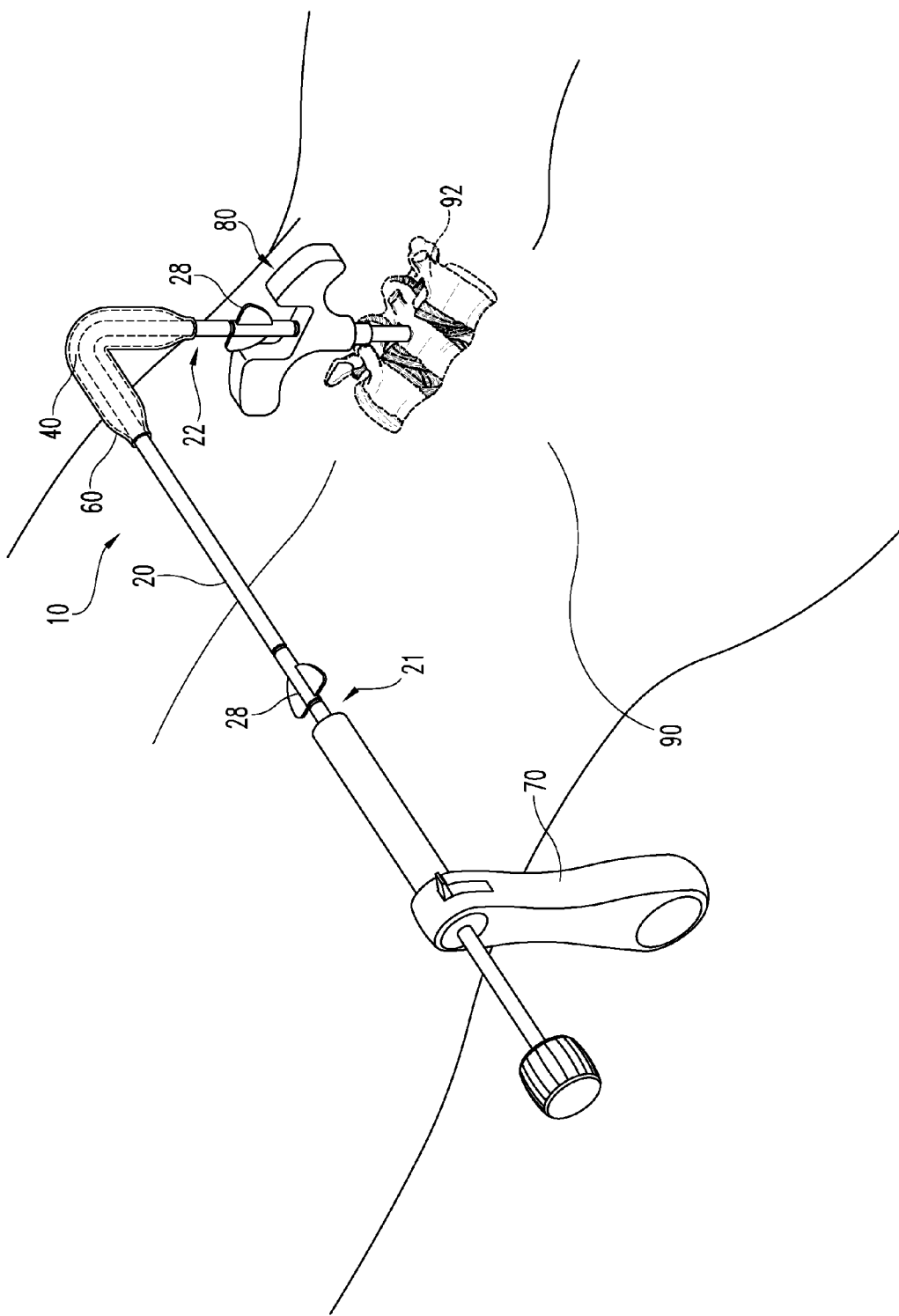
FIG. 8 is a perspective view of a pressure sensing tube utilized as a vertebroplasty extension tube connecting a cement injector to an intraosseous needle inserted into a person.

Referring to FIG. 8, a pressure sensing tube is illustrated as a vertebroplasty extension tube connecting cement injector 70 to intraosseous needle 80 (that is illustrated inserted through body 90 into vertebral body 92). Pressure sensing tube 10 includes pressure sensing material 40 and outer member 60 positioned on distal end 22 of tube 20. This positions pressure sensitive material 40 proximate to intraosseous needle 80 that may provide an improved indication of excessive injection pressure within intraosseous 80 and vertebral body 92 compared to other locations along pressure sensing tube 10. Vertebroplasty extension tube 10 is connected to cement injector 70 and intraosseous needle 80 by connectors 28 on proximal end 21 and distal end 22.

In the embodiment illustrated in FIG. 8, the interventionalist inserts intraosseous needle 80 into a compromised vertebral body. A multi-compound cement is prepared by combining and mixing constituent components together and filling cement injector 70 with the mixed cement. Pressure sensing tube 10 is connected to cement injector 70 using a lure-lock connector 28. Cement injector 70 is actuated to purge any air or gas from cement injector 70 and pressure sensing tube 10. Pressure sensing tube 10 is next connected to the previously inserted intraosseous needle using the second lure-lock connector 28. The interventionalist then injects cement into compromised vertebral body 92 while observing vertebral body 92 under fluoroscopy or some other form of visualization while remaining outside of the field of the fluoroscopy or other form of visualization. With pressure sensing tube 10, the interventionalist also monitors whether excessive injection pressure is developed at intraosseous needle 80 by observing the visual appearance of pressure sensitive material 40. In the event intraosseous needle 80, vertebral body 92 or pressure sensing tube 10 becomes occluded, for example by set-up cement, the interventionalist is warned of the condition and the current injection can be stopped.

In alternative embodiments, cement injector 70 may include any type of injector operable to eject a viscous medical fluid and intraosseous needle 80 may include any type of needle or catheter operable to inject the viscous medical fluid into any intraosseous space including bones other than vertebral bodies. Thus, pressure sensing tubing 10 may be used to monitor excessive injection pressure of any viscous medical fluid injected through any type of needle or catheter anywhere into a intraosseous space in a medical procedure. What constitutes excessive injection pressure for a particular medical procedure is related to the injection environment of the particular medical procedure. As discussed above, the characteristics of pressure sensing tubing 10 can be selected based on the desired indicative pressure for pressure sensing tubing 10.

While the disclosure has been illustrated and described in detail in the drawings and foregoing description, the same is to be considered as illustrative and not restrictive in character, it being understood that only the preferred embodiments have been shown and described and that all changes and modifications that come within the spirit of the disclosure are desired to be protected. It is to be understood that aspects of this disclosure described with respect to particular embodiments or associated parts can be included or used with other embodiments or parts.

I claim:

1. An injection assembly comprising:
   an injection apparatus constructed and arranged to eject a flowable therapeutic liquid;
   a pressure sensing extension tube comprising:
      a proximal end removably coupled to the injection apparatus;
      a distal end;
      an inner tube defining a first lumen, wherein the inner tube is deformable in response to a change in pressure in the first lumen and wherein the first lumen is constructed and arranged to convey the flowable therapeutic liquid from the proximal end to the distal end through the first lumen;
      an outer member; and
      a pressure-indicating film positioned between the inner tube and the outer member, wherein the pressure-indicating film is adapted to display a differing visual appearance when the inner tube deforms to compress the pressure-indicating film between the inner tube and the outer member.

2. The assembly of claim 1, wherein the outer member is less compliant than the inner tube.

3. The assembly of claim 1, wherein the inner tube, the pressure-indicating film and the outer member are configured and arranged such that the differing visual appearance displayed by the pressure-indicating film is correlated to a predetermined first lumen pressure.

4. The assembly of claim 3, wherein the injection apparatus is configured and arranged as a bone cement injector, wherein the flowable therapeutic liquid is a bone cement, and wherein the pressure sensing extension tube is configured and arranged as a vertebroplasty extension tube.

5. The assembly of claim 3, wherein the predetermined first lumen pressure is greater than 3000 psi.

6. The assembly of claim 1, wherein the inner tube comprises a wall that is continuous and uninterrupted both around the periphery of the first lumen and between the proximal and distal ends of the pressure sensing extension tube.

7. The assembly of claim 1, wherein the pressure-indicating film permanently changes its visual appearance when it displays the differing visual appearance.

8. The assembly of claim 1, wherein the pressure-indicating film further comprises a plurality of micro-capsules each containing a color-forming material, wherein the micro-capsules are constructed and arranged to rupture and release the color-forming material when pressure-indicating film is compressed.

9. The assembly of claim 1, further comprising a first medical device connector on said proximal end of said pressure sensing extension tube and a second medical device connector on said distal end of said pressure sensing extension tube.

10. The assembly of claim 9, wherein said first and second medical device connectors are Luer Taper connectors.

11. The assembly of claim 1, wherein the outer member comprises translucent thermoplastic heat-shrink tubing shrunk over the inner tube and the pressure sensitive material.

12. A method of manufacturing a pressure sensing extension tube comprising:
    positioning a pressure-indicating film on the outer surface of an extension tube having a first lumen; and
    covering the pressure-indicating film and at least a portion of the extension tube with an outer member, wherein the pressure-indicating film is restrained between the outer surface of the extension tube and the inner surface of the translucent outer member and wherein the pressure-indicating film is adapted to permanently change its visual appearance when compressed between the extension tube and the outer member.

13. The method of claim 12, further comprising spirally wrapping the pressure-indicating film around the outer surface of the extension tube.

14. The method of claim 12, further comprising longitudinally rolling the pressure-indicating film around the outer surface of the extension tube.

15. The method of claim 12, further comprising heat-shrinking a translucent thermoplastic heat-shrink outer member over the extension tube and the pressure-indicating film.

16. The method of claim 12, further comprising positioning the pressure-indicating film on a distal portion of the extension tube.

17. The method of claim 12, further comprising configuring and arranging the extension tube and the outer member such that the permanent change in visual appearance correlates to a predetermined pressure in the first lumen.

18. The method of claim 12, wherein the pressure-indicating film comprises a plurality of micro-capsules each containing a color-forming material that are constructed and arranged to rupture and release the color-forming material when the pressure-indicating film is compressed between the extension tube and the outer member.

19. A pressure indicating extension tube comprising:
    an extension tube defining a lumen and including a first degree of deformability such that a change in pressure in the lumen changes the shape of the extension tube;
    a pressure-indicating film external of the extension tube; and
    a translucent thermoplastic heat-shrink tube shrunk over the pressure-indicating film, wherein the pressure-indicating film is adapted to permanently change its color when compressed between the heat-shrink tube and the extension tube.

20. The pressure sensitive extension tube of claim 19, wherein the pressure-indicating film further comprises a plurality of micro-capsules each containing a color-forming material, wherein the micro-capsules are constructed and arranged to rupture and release the color-forming material when the pressure-indicating film is compressed.

* * * * *